United States Patent
Geissler

(10) Patent No.: US 7,582,316 B1
(45) Date of Patent: Sep. 1, 2009

(54) KETONE-STEROID EXTRACTS FROM THE CISSUS QUADRANGULARIS PLANT AND METHODS THEREOF

(76) Inventor: Jacob Geissler, 3941 Waterford Way, Denton, TX (US) 76210

( * ) Notice: Subject to any disclaimer, the term of this patent is extended or adjusted under 35 U.S.C. 154(b) by 30 days.

(21) Appl. No.: 11/459,328

(22) Filed: Jul. 21, 2006

Related U.S. Application Data

(60) Provisional application No. 60/595,630, filed on Jul. 21, 2005.

(51) Int. Cl.
*A61K 36/00* (2006.01)
(52) U.S. Cl. .............................. 424/773; 424/725
(58) Field of Classification Search .................. None
See application file for complete search history.

(56) References Cited

U.S. PATENT DOCUMENTS 7,175,859 B1 * 2/2007 Oben ..................... 424/725
2004/0156920 A1 * 8/2004 Kane ..................... 424/725
2005/0048141 A1 * 3/2005 Cortes et al. ............. 424/725
2005/0084547 A1 * 4/2005 Subbiah ................. 424/740

* cited by examiner

*Primary Examiner*—Christopher R. Tate
(74) *Attorney, Agent, or Firm*—Kramer, Levin, Naftalis & Frankel LLP

(57) ABSTRACT

A method and composition made from extraction of the roots of *Cissus Quadrangularis* Linn plant is disclosed. The method comprises washing, drying and grinding the roots to provide a powdered root. A first solvent is added to the powdered root to extract a mixture comprising one or more keto-steroids and impurities. A second solvent is added to the mixture of the partially extracted powdered root and first solvent, wherein the one or more keto-steroids is substantially soluble in the second solvent and the impurities are soluble in the first solvent. A highly purified composition obtained by the method may be further combined with at least one excipient to provide a high yield keto-sterone composition having a predetermined keto-sterone content. A dose of the keto-sterone composition may be administered to a person to promote lean body mass, treat damaged or diseased connective tissue and provide an analgesic effect while reducing cortisol.

15 Claims, No Drawings

KETONE-STEROID EXTRACTS FROM THE CISSUS QUADRANGULARIS PLANT AND METHODS THEREOF

This application claims priority based on Provisional Application No. 60/595,630, filed on Jul. 21, 2005, 37 USC § 120

FIELD OF THE INVENTION

This invention relates generally to extracts of the *Cissus Quadrangularis* Linn plant (hereinafter *Cissus q*.) and more specifically to compositions and methods for preparing a ketone-steroid extract from a ground powder of the *Cissus q.* plant root, and the use of the *Cissus q.* to promote the healing of connective tissue such as those that form tendons, ligaments, cartilage and fascia, promote lean body mass, induce analgesia, and lower cortisol levels.

BACKGROUND OF THE INVENTION

In the past Chopra et al., reported that *Cissus q.* is able to speed bone healing when they showed it acts as a glucocorticoid antagonist (see for example: Chopra, S. S., Patel, M. R., Awadhiya, R. P. 64(9) Indian J. Med. Res. 1365-8 (1976) and Chopra, S. S., et al., 63(6) Indian J. Med. Res. 824-8 (1976)). Since anabolic/androgenic compounds are well known to act as antagonists to the glucocorticoid receptor as well as to promote bone growth and fracture healing, several groups have postulated that *Cissus q.* may possess anabolic and/or androgenic properties (see for example: Chopra, S. S., Patel, M. R., Awadhiya, R. P. 64(9) Indian J. Med. Res. 1365-8 (1976); Shirwaikar, A., Khan, S., Malini, S., 89(2-3) J. Ethnopharmacol. 245-50 (2003)).

In addition to speeding the remodeling process to heal bone, *Cissus q.* also may lead to a much faster increase in bone tensile strength. In clinical trials *Cissus q.* has led to a fracture healing time on the order of 33 to 55 percent of that for controls. A number of studies where bones were weakened by treatment with cortisol were modified by administering *Cissus q.* extract. As a result of this modification, the cortisol induced weakening was halted, and the healing process began, thereby suggesting that *Cissus q.* exerts antiglucocorticoid properties. Similarly to forskolin and green tea, *Cissus q.* lacks any stimulatory effect so it may be appropriate for nighttime use.

While the increased rate of bone healing may be of great significance to persons suffering from chronic diseases like osteoporosis, (see for example: Combaret, L., et al. 378 (Pt 1) Biochem J. 239-46 (2004)), the antiglucocorticoid properties of *Cissus q.* may be of greater interest to the average bodybuilder or athlete, since endogenous glucocorticoids, particularly cortisol, are not only catabolic to bone, but catabolize muscle tissue as well. Numerous studies over the years have suggested that glucocorticoids, including the body's endogenous hormone cortisol, activate pathways that degrade not only bone, but skeletal muscle tissue as well. A recently published report documented exactly how glucocorticoids (including cortisol) induce muscle breakdown. In particular, they activate the so-called ubiquitin-proteasome pathway of proteolysis. This pathway of tissue breakdown is important for removing damaged and non-functional proteins. However, when it is overactive during periods of elevated cortisol (e.g., disease states, stress, and overtraining) excess amounts of normal tissue may be broken down as well. By exerting an anabolic, antiglucocorticoid effect *Cissus q.* may help to preserve muscle tissue during times of physical and emotional stress.

It has also been shown that *Cissus q.* possesses analgesic properties on a mg per mg basis comparable to aspirin or anti-inflammatory drug such as ibuprofen and the like. In particular, *Cissus q.* has been shown to be highly effective in the relief of pain, the reduction of swelling and the promotion of the process of healing of simple fractures as well as in the cure of allied disorders associated with bone fractures. However, the mechanism through which *Cissus q.* exerts its analgesic and anti-inflammatory properties has not been well characterized. It is believed that it may act centrally, or by preventing the conversion of arachidonic acid to inflammatory prostaglandins. For these reasons, it may be used to maintain the healthy function of bones and joints, and to treat osteoarthritis, rheumatoid arthritis, and osteoporosis.

While *Cissus q.* may act to improve bone healing, as suggested by most of the published literature, it may also provide an improved healing rate for connective tissue in general, including tendons. Such an improvement would provide an enhanced benefit to bodybuilders and athletes.

SUMMARY OF THE INVENTION

The current disclosure provides for compositions and methods of providing extracts of *Cissus q.* which improve the healing rate of damaged connective tissue, promote lean body mass, maintain healthy bones and joints, or treating osteoarthritis, rheumatoid arthritis, or osteoporosis, induce analgesia, and reduce cortisol.

In accordance with an embodiment of this invention, a method of preparing a high yield *Cissus Quadrangularis* keto-sterone composition from a *Cissus q.* plant is disclosed. In a step of the method one or more roots of a *Cissus q.* plant are washed, dried and ground to a root powder. In other steps, a first solvent is added to the root powder of the *Cissus q.* plant to provide a first mixture of root extracts and the first solvent followed by adding a second solvent to the first mixture to provide a second mixture comprising the first mixture and the second mixture. Substantially one or more keto-sterones of the first mixture is insoluble in the second solvent and a quantity of one or more impurities of the first mixture is soluble in the second solvent. In other steps a quantity of substantially one or more keto-sterones is separated from the quantity of the one or more impurities of the second mixture, and a quantity of the substantially one or more keto-sterones is combined with at least one physiologically acceptable carrier or excipient to produce the high yield *Cissus Quadrangularis* keto-sterone composition having a predetermined keto-sterone content.

In further steps the at least a quantity of the substantially one or more keto-sterones may be filtered from the second mixture to provide a paste comprising a purified quantity of the substantially one or more keto-sterones, and a quantity of the first solvent to the paste may be added to produce a solution of the paste and the first solvent. Furthermore, a quantity of the second solvent may be added to the solution of the paste and the first solvent to produce a purer paste after filtration, and repeated subsequent addition of first and second solvents to subsequently purer pastes of the substantially one or more keto-sterones followed by filtration may provide one or more subsequently even purer pastes of the substantially one or more keto-sterones to obtain a predefined highly purified substantially one or more keto-sterones composition of *Cissus Quadrangularis*.

In accordance with another embodiment of this invention, a method of promoting lean body mass, treating damaged or diseased connective tissue, maintaining bone and joint function, treating osteoarthritis, rheumatoid arthritis, or osteoporosis, providing an analgesic effect, or reducing cortisol in a person is disclosed. A *Cissus Quadrangularis* keto-sterone composition is provided, the composition being made by washing, drying and grinding one or more roots of a *Cissus q.* plant to a root powder; adding a first solvent to the root powder of the *Cissus q.* plant to provide a first mixture of root extracts and the first solvent; adding a second solvent to the first mixture to provide a second mixture comprising the first mixture and the second mixture, wherein substantially one or more keto-sterones of the first mixture is insoluble in the second solvent and a quantity of one or more impurities of the first mixture is soluble in the second solvent; separating a quantity of substantially one or more keto-sterones from the quantity of the one or more impurities of the second mixture; and combining a quantity of the substantially one or more keto-sterones with at least one physiologically acceptable carrier or excipient to produce the high yield *Cissus Quadrangularis* keto-sterone composition having a predetermined keto-sterone content. In a further step a dose of the *Cissus Quadrangularis* keto-sterone composition is administered to the person.

The dose may be a daily dose of about 2 grams to about 8 grams of the *Cissus Quadrangularis* keto-sterone composition, or a daily dose of about 3 grams to about 6 grams of the *Cissus Quadrangularis* keto-sterone composition. The dose may divided into a plurality of individual doses of the *Cissus Quadrangularis* keto-sterone composition.

The foregoing and other articles, features, and advantages of the invention will be apparent from the following more detailed description of the preferred embodiments of the invention. The various features may be utilized or claimed alone or in any combination.

DESCRIPTION OF THE INVENTION

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

In the Summary above, the Description of the Invention, and the Claims and Abstract below, reference may be made to particular features (including method steps) of the invention. It is to be understood that this disclosure includes possible combinations of such particular features. For example, where a particular feature is disclosed in the context of a particular aspect or embodiment of the invention, or a particular claim, that feature may also be used, to the extent possible, in combination with and/or in the context of other particular aspects and embodiments of the invention, and in the invention generally.

The term "comprises" and grammatical equivalents thereof are used herein to mean that other components, ingredients, steps etc. are optionally present. For example, an article "comprising" (or "which comprises") components A, B and C can consist of (i.e. contain only) components A, B and C, or can contain not only components A, B and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number or the indefinite article "a" (meaning "one") is used herein to denote the start of a range beginning with that number (which may be a range having an upper limit or no upper limit, depending on the variable being defined). For example "at least one" or "at least a" means 1 or more than 1. The term "at most" followed by a number is used herein to denote the end of a range ending with that number (which may be a range having 1 or 0 as its lower limit or a range having no lower limit, depending upon the variable being defined). For example, "at most 4" means 4 or less than 4, and "at most 40%" means 40% or less than 40%. If, in this disclosure, a range is given as "(a first number) to (a second number)" or "(a first number)-(a second number)", this means a range whose lower limit is the first number and whose upper limit is the second number. For example, 0-10 mm means a range whose lower limit is 0 mm, and whose upper limit is 10 mm.

The term "or" is used herein as a conjunction used to link alternatives in a series of alternatives. The term "and/or" is used herein as a conjunction meaning that either or both of two options may be valid.

Certain effects of *Cissus q.* extract have been observed but their specific method of action has not been determined. Without limiting the current disclosure, *Cissus q.* extract may promote an increase in lean body mass since glucocorticoids induce the breakdown of skeletal muscle tissue by antagonizing the catabolic action of glucocorticoids on muscle tissue. Furthermore, the conversion of arachidonic acid to inflammatory prostaglandins may be inhibited since *Cissus q.* extract induces analgesia. Additionally, *Cissus q.* extract may promote healing of injured connective tissue such as tendons, ligaments, and muscular fascia acts by blocking the catabolic action of glucocorticoids on connective tissue. Advantageously, *Cissus q.* extract may be suitable for maintenance of the proper function of bones and joints, and the treatment of osteoarthritis, rheumatoid arthritis, and osteoporosis.

*Cissus q.* (also known as Sugpon-sugpon) is an ancient medicinal plant native to the hotter parts of Ceylon and India and also in Cagayan, Batangas and Rizal Provinces in Luzon; in Negros; in Cebu; and in Siquijor, in dry thickets in and about towns at low altitudes. It is occasionally planted and is also found in areas ranging from tropical India to tropical Africa and Java.

The plant is a smooth vine with fleshy, green, stout, 4-angled stems which are 1 to 1.5 centimeters thick and much contracted at the nodes. The internodes, one from each node broadly ovate or triangular-reniform 4 to 6 centimeters long, somewhat fleshy distantly toothed with small, appressed, sharp teeth, blunt at the tip, and broad and heart-shaped at the base. The flowers are pinkish, about 2.5 millimeters long, and borne on small axillary cymes. The fruit is rounded, fleshy, and succulent. The powdered root of the plant was prescribed in the ancient Ayurvedic texts as a general tonic and analgesic, with specific bone fracture healing properties.

Exemplary Methods for Extracting Keto-sterone (or Ketone-steroid) from *Cissus q.*

Initially, it has been determined that the content of keto-sterone in a *Cissus q.* plant varies substantially with location, climatic conditions, mode of irrigation and age of the plant. Keto-sterone (or ketone-steroid) may comprise between about 0.1 to 0.5% or less of the plant. Consequently, a large quantity (for example, about 100 kilograms) of powdered plant root is extracted in order to get an appreciable yield of the root extract.

In a step of the method, before extracting the roots of the *Cissus q.* plant to obtain keto-sterone and other products (hereinafter termed root extract), the roots are washed with water, dried and ground to a powder. Although a *Cissus q.* plant extract may be obtained in a number of different ways the extraction method described below is believed to provide a number of economical benefits.

In a further step of the method, the roots are extracted using a first suitable solvent. Without limiting the disclosure, examples of first suitable solvents include toluene, methanol, ethanol, chloroform, ethyl acetate, ethylene dichloride, and the like. In an embodiment of the method, a mixture of toluene and methanol in a volume ratio of about 100:1 to about 100:2 is suitable and in an exemplary embodiment the volume ratio of mixture of toluene and methanol is about 100:1.

Multiple solvent extractions of the roots of *Cissus q.* may be made. The volume of solvent mixture and the number of extraction cycles may depend on the type of extractor used. Without limiting the disclosure, and solely to illustrate an example of the method, about 10 volumes of a toluene and methanol solvent mixture may be used in a continuous-type solvent extractor such as a Soxhlet extractor.

In an embodiment of the method, extraction with the first solvent may be implemented at a temperature ranging from about 35° C. to about 105° C. In an exemplary embodiment the temperature range is between about 50° C. to about 75° C. Of course the extraction time depends on the volume of root extracted as well as the extraction temperature, and in an exemplary embodiment the extraction time is about 6 hours. A further variable which may influence the efficiency of the extraction is applied pressure. Thus, a 1 kilogram pressure increase has been found to increase extraction efficiency.

In an embodiment, after multiple extractions with the above-described solvent mixture to provide an appreciable yield, the solvent mixture comprising the root extracts may be combined, filtered and concentrated under vacuum at low temperatures. In one embodiment the temperature for concentration of the root extracts may be less than about 60° C. In an exemplary embodiment, the root extract may be concentrated with a thin film evaporator, rotary film evaporator or agitated wiped film evaporator, and the like as is understood in the art to avoid decomposition of the keto-sterone, which is temperature sensitive. After substantial solvent removal the root extract has the form of a paste.

In another exemplary aspect of the method, toluene may be added to the paste. According to an aspect of the method a minimum amount of the first solvent (such as toluene) may be added to the paste to substantially dissolve the keto-sterone (or ketone-steroid) components. Of course, when configured to reduce the first solvent quantity to a predetermined level, no solvent may need to be added to the paste.

In an embodiment of the method, the paste comprises the sought after one or more ketone-steroid components and a quantity of one or more impurities. The one or more impurities may be separated from the root extract by combining the dissolved root extracts and first solvent with a second solvent. In one aspect of the method, the *Cissus q.* extract component comprising the one or more keto-sterones is insoluble in the second solvent and the impurities are soluble in the second solvent. Thus, the one or more impurities remain in solution in the second solvent, while the one or more keto-sterones separate from the second solvent.

Without limiting the disclosure, any solvent in which the one or more keto-sterones root extract is insoluble may comprise the second solvent. Of course, the second solvent may be chosen so that a large quantity of the one or more impurities associated with the extract are soluble, so that the resultant one or more keto-sterones obtained in this second step is substantially purer than in the first solvent root extract. In an exemplary embodiment, the second solvent may comprise a substantially non-polar solvent such as petroleum ether (having a boiling point in the range of about 60° C. to about 80° C.).

In an embodiment of a step of the method, the second solvent may be combined with the root extract and first solvent mixture so that the ratio of the first solvent to the second solvent ranges from about 1:10 to about 1:20. In an exemplary embodiment the first solvent to second solvent ration may be about 1:20. In an exemplary embodiment of a step of the method, the mixture of root extract, first solvent and second solvent may be agitated at a temperature ranging from about 40° C. to about 60° C. for a few hours (more particularly about 2 hours). According to observations while implementing this method, the one or more keto-sterone appears to be insoluble at the above temperature and solvent ratio.

In one or more purification steps of the method, the one or more keto-sterones may be thereafter collected (for example, by filtration) as a paste and a filtrate. The collected paste may be re-dissolved in a minimum quantity of the first solvent, and the second solvent may be added thereafter to the mixture of collected paste and the first solvent to further purify the collected paste. In an exemplary embodiment of the re-dissolving step, the ratio of the first solvent to the second solvent may be about 1:25 and again agitated at a temperature ranging from 40° C. to about 60° C. for a few hours (more particularly about 2 hours). Of course, the purification process may be repeated iteratively to obtain one or more keto-sterones with any level of purity. Furthermore, the second solvent may be added to the filtrate comprising the one or more impurities, the first and second solvent and any of the one or more keto-steroids that had not previously separated. Subsequently, any further paste may be separated as described above, and further purified as described above.

In an exemplary embodiment of the one or more purification steps three iterations provide about 15% to about 20% by weight of one or more keto-sterones. It is understood that higher purities may be obtained as described above. The product preferably contains from about 15% to about 40% of the one or more keto-sterones, although, of course, the process uniquely may provide substantially 100% purified one or more keto-sterones. In an exemplary embodiment of the method, a yield of about 1.5 kilograms of one or more keto-sterones may be extracted from 100 kilograms of *Cissus Quadrangularis* Linn root.

Since the one or more keto-sterones are significantly hygroscopic, and inconvenient to use, the method comprises at least on further step. In an exemplary embodiment the one or more keto-sterones root extracts may be combined with at least one physiologically acceptable carrier (or excipient) to provide a keto-sterone composition having a predetermined keto-sterone content. In an exemplary embodiment the one or more excipient may comprise magnesium oxide, magnesium carbonate, dicalcium phosphate, mixtures thereof and the like. Of course, the quantity of excipients depends on the desired predetermined one or more keto-sterones component content.

In a further step of the method, standardization of about 1% to about 40% purity of the one or more keto-sterones component may be achieved although it is understood that depending on the specific need, a product may be upgraded to comprise up to substantially 100% purity of the one or more keto-sterones component. In an embodiment of the method, in one or more steps, standardization may be accomplished with column chromatography, followed by re-crystallization of appropriate fractions obtained from the column. In one embodiment of the standardization steps the appropriate fractions may comprise about 5% to about 20% of one or more keto-sterones. In a further embodiment the appropriate fractions may comprise about 8 to about 15% and in an exemplary embodiment the appropriate fractions may comprise about 10% of one or more keto-sterones.

Characterization of the Keto-Sterone (or Ketone Steroid) Root Extract from *Cissus q*.

Keto-sterone compositions prepared by any of the above methods were found to be stable. Composition stability was determined under normal ambient storage conditions, as well as accelerated storage conditions. During this study, quality of the keto-sterone compositions was tested using stability indicating parameters such as degradation products identified by appropriate chromatographic and spectral techniques as is known in the art. Such studies revealed the keto-sterone root extracts obtained by the methods described above were stable for a period of not less than 5 years, when stored under ambient storage conditions.

Without limiting the disclosure, some physical properties of an example keto-sterone composition prepared according to the method describe above are shown in Table 1 below:

TABLE 1

Some Physical Properties of an Example Keto-sterone Composition Root Extract from Cissus q.

| | |
|---|---|
| Appearance | Brown powder |
| Odor | Characteristic wheat bread odor |
| Thin Layer Chromatography | Complies with a standard |
| Weight loss on Drying | Not greater than 10% |
| Water Solubility | Insoluble |
| Ethanol Solubility | Not less than 45% |
| Heavy Metals | Not greater than 2 parts per million |
| Arsenic | Not greater than 1 part per million |
| Lead | Not greater than 4 parts per million |
| Bulk Density | About 0.4 to about 0.7 grams/milliliter |
| Particle Size | Not less than 100% passes through 20 size mesh; Not less than 75% passes through 40 size mesh; Not less than 50% passes through 80 size mesh. |
| HPLC | Between about 10% and 11% |

Method of Administering the Keto-Sterone (or Ketone Steroid) Root Extract

In the one or more embodiments of a method to promote induction of lean body mass and to induce analgesia, a *Cissus q*. root extract obtained by any method described above should be administered in a daily dose of from about 2 grams to about 8 grams. The dose may be administered orally. Of course, other ingredients such as sweeteners, colorants and the like may be added to the dose. Furthermore, in an exemplary embodiment the daily dose may comprise about 3 grams to about 6 grams of the above described *Cissus q*. extract. In a further exemplary embodiment, the daily dose may be divided into a plurality of individual doses rather than a single dose. As a matter of convenience, in order to promote a tendency to create a lean body mass and/or to heal injured or diseased connective tissue, three individual doses of *Cissus q*. may be adequately effective. Such connective tissue may include a person's tendons, ligaments, cartilage, muscle fascia and the like. Furthermore, the administration of the above described dosages of *Cissus q*. root extract may reduce a person's cortisol levels and promote analgesia. Without limiting this disclosure, diseases such as rheumatoid arthritis, osteoarthritis, osteoporosis and the like may benefit from administering the doses described above.

While the invention has been particularly shown and described with reference to preferred embodiments thereof, it will be understood by those skilled in the art that the foregoing and other changes in form and details may be made therein without departing from the spirit and scope of the invention. The scope of the present invention is not intended to be limited by the specific examples set out herein, but rather is to be interpreted according to the following claims.

What is claimed is:

1. A method of preparing a high yield *Cissus quadrangularis* keto-sterone composition from a *C. quadrangularis* plant comprising the steps of:
    washing, drying and grinding one or more roots of a *C. quadrangularis* plant to a root powder;
    adding a first solvent to the root powder of the *C. quadrangularis* plant to provide a first mixture of root extracts and the first solvent, wherein the first solvent is selected from the group consisting of toluene, methanol, ethanol, chloroform, ethyl acetate, ethylene dichloride and mixtures thereof;
    adding a second solvent to the first mixture to provide a second mixture comprising the first mixture and the second mixture, wherein substantially one or more keto-sterones of the first mixture is insoluble in the second solvent and a quantity of one or more impurities of the first mixture is soluble in the second solvent, and wherein the second solvent is a substantially non-polar solvent;
    separating a quantity of substantially one or more keto-sterones from the quantity of the one or more impurities of the second mixture; and
    combining a quantity of the substantially one or more keto-sterones with at least one physiologically acceptable carrier or excipient to produce the high yield *C. quadrangularis* keto-sterone composition having a predetermined keto-sterone content.

2. The method of claim 1 further comprising the steps of:
    filtering the at least a quantity of the substantially one or more keto-sterones from the second mixture to provide a paste comprising a purified quantity of the substantially one or more keto-sterones;
    adding a quantity of the first solvent to the paste to produce a solution of the paste and the first solvent;
    adding a quantity of the second solvent to the solution of the paste and the first solvent to produce a purer paste after filtration; and
    repeating subsequent addition of the first and second solvents to subsequently purer pastes of the substantially one or more keto-sterones followed by filtration to provide one or more subsequently even purer pastes of the substantially one or more keto-sterones to obtain a predefined highly purified substantially one or more keto-sterones composition of *C. quadrangularis*.

3. The method of claim 1 wherein the root powder of a *C. quadrangularis* plant has a keto-sterone content between about 0.1% to about 0.5% by weight.

4. The method of claim 1 wherein the second solvent comprises a petroleum ether having a boiling point of about 60° C. to about 80° C.

5. The method of claim 1 wherein the first solvent comprises a mixture of toluene and methanol.

6. The method of claim 1 wherein the powdered roots are extracted with the first solvent at a temperature ranging from about 35° C. to about 105° C.

7. The method of claim 1 wherein about 100 kilograms of the powdered roots are extracted with the first solvent for about 6 hours.

8. The method of claim 1 wherein the ratio of the first solvent to the second solvent ranges from about 1:10 to about 1:20 by volume.

9. The method of claim 1 wherein a mixture of about 100 kilograms of root powder, the first solvent and the second solvent are agitated at a temperature ranging from about 40° C. to about 60° C. for about 2 hours.

10. A *Cissus. quadrangularis* keto-sterone composition made by:
   washing, drying and grinding one or more roots of a *C. quadrangularis* plant to a root powder;
   adding a first solvent to the root powder of the *C. quadrangularis* plant to provide a first mixture of root extracts and the first solvent, wherein the first solvent is selected from the group consisting of toluene, methanol, ethanol, chloroform, ethyl acetate, ethylene dichloride and mixtures thereof;
   adding a second solvent to the first mixture to provide a second mixture comprising the first mixture and the second mixture, wherein substantially one or more keto-sterones of the first mixture is insoluble in the second solvent and a quantity of one or more impurities of the first mixture is soluble in the second solvent, and wherein the second solvent is a substantially non-polar solvent;
   separating a quantity of substantially one or more keto-sterones from the quantity of the one or more impurities of the second mixture; and
   combining a quantity of the substantially one or more keto-sterones with at least one physiologically acceptable carrier or excipient to produce the high yield *C. quadrangularis* keto-sterone composition having a predetermined keto-sterone content.

11. A method of promoting lean body mass, treating damaged or diseased connective tissue, providing an analgesic effect, maintaining healthy bones and joints, or treating osteoarthritis, rheumatoid arthritis, or osteoporosis, inducing analgesia, or reducing cortisol in a person comprising:
   administering a dose of *Cissus Quadrangularis* keto-sterone composition to said person said composition comprising the *C. quadrangularis* keto-sterone composition made by:
   washing, drying and grinding one or more roots of a *C. quadrangularis* plant to a root powder;
   adding a first solvent to the root powder of the *C. quadrangularis* plant to provide a first mixture of root extracts and the first solvent, wherein the first solvent is selected from the group consisting of toluene, methanol, ethanol, chloroform, ethyl acetate, ethylene dichloride and mixtures thereof;
   adding a second solvent to the first mixture to provide a second mixture comprising the first mixture and the second mixture, wherein substantially one or more keto-sterones of the first mixture is insoluble in the second solvent and a quantity of one or more impurities of the first mixture is soluble in the second solvent, and wherein the second solvent is a substantially non-polar solvent;
   separating a quantity of substantially one or more keto-sterones from the quantity of the one or more impurities of the second mixture; and
   combining a quantity of the substantially one or more keto-sterones with at least one physiologically acceptable carrier or excipient to produce the high yield *C. quadrangularis* keto-sterone composition having a predetermined keto-sterone content.

12. The method of claim 11 wherein the dose is a daily dose of about 2 grams to about 8 grams of the *C. quadrangularis* keto-sterone composition.

13. The method of claim 11 wherein the dose is a daily dose of about 3 grams to about 6 grams of the *C. quadrangularis* keto-sterone composition.

14. The method of claim 11 wherein the dose is divided into a plurality of individual doses of the *C. quadrangularis* keto-sterone composition.

15. The method of claim 14 wherein the plurality of individual doses of the *C. quadrangularis* keto-sterone composition is three.

* * * * *